United States Patent [19]

Holland et al.

[11] 4,273,115

[45] Jun. 16, 1981

[54] MOLDABLE PLASTIC ORTHOPEDIC CAST

[75] Inventors: Kenneth M. Holland, Pebble Beach; Milton F. Custer, Livermore, both of Calif.

[73] Assignee: Hexcel Corporation, Dublin, Calif.

[21] Appl. No.: 102,285

[22] Filed: Dec. 10, 1979

Related U.S. Application Data

[63] Continuation of Ser. No. 20,006, Mar. 12, 1979, abandoned, which is a continuation of Ser. No. 633,333, Nov. 19, 1975, abandoned.

[51] Int. Cl.$^3$ .............................................. A61F 5/04
[52] U.S. Cl. ..................................................... 128/90
[58] Field of Search ................ 128/89 R, 90, 155, 156

[56] References Cited

U.S. PATENT DOCUMENTS

| | | | |
|---|---|---|---|
| 3,618,599 | 11/1971 | Beightol | 128/90 |
| 3,669,708 | 6/1972 | Reber et al. | 128/90 |
| 3,692,023 | 9/1972 | Phillips et al. | 128/90 |
| 3,881,473 | 5/1975 | Corvi et al. | 128/90 |

Primary Examiner—John D. Yasko

[57] ABSTRACT

Orthopedic structures are prepared from a thermal softening resin (e.g. polycaprolactone) impregnated large mesh knit fabric carrier having relatively large diameter strands and having a relatively high weight ratio of the polycaprolactone or equivalent resin composition to the fabric carrier. The impregnated fabric can be formed in rolls which may be warmed above the softening temperature of the resin. The thermally softened impregnated fabric becomes highly flexible and pliant and may then be wrapped in multiple layers about the limb to be immobilized. The large knit fabric carrier allows for twisting of the fabric, forming and reforming, so as to obtain the desired shape and degree of support. The overlapping layers of impregnated fabric bond to each other during wrapping and whereafter the impregnated fabric rapidly cools to a hard structurally stable cast, which is porous so as to minimize maceration or other deleterious skin conditions from developing.

13 Claims, 5 Drawing Figures

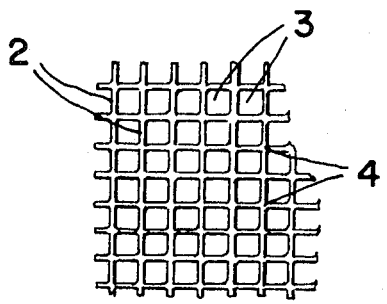
FIG_1
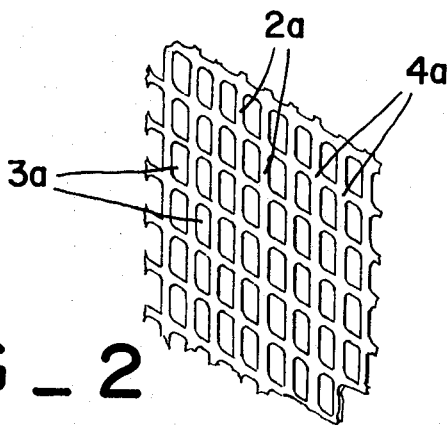
FIG_2
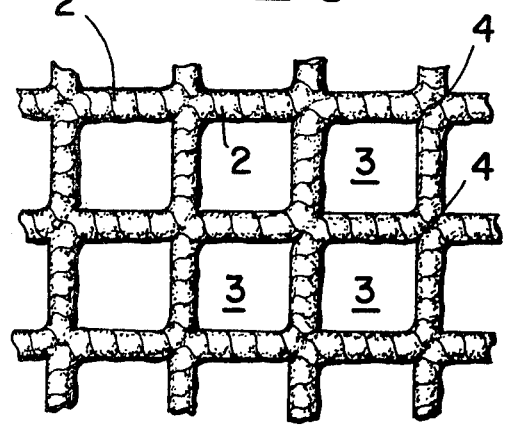
FIG_3
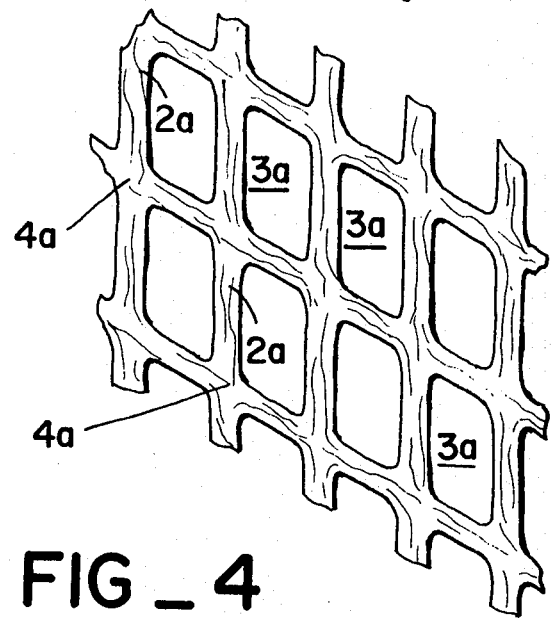
FIG_4
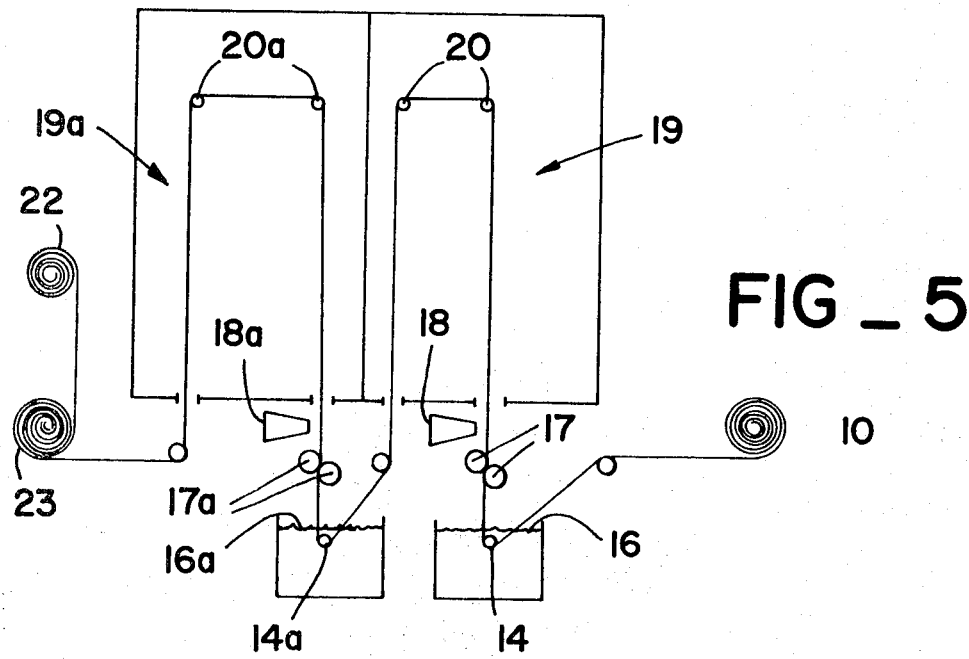
FIG_5

MOLDABLE PLASTIC ORTHOPEDIC CAST

This is a continuation, of application Ser. No. 20,006, filed Mar. 12, 1979, now abandoned, the latter application being a continuation of application Ser. No. 633,333, filed Nov. 19, 1975, now abandoned.

BACKGROUND OF THE INVENTION

1. Field of the Invention

Orthopedic structures find wide use in the immobilization of limbs in aiding the healing process. In the maintenance of fixation of fractured bones, immobilization of inflamed or injured joints, in cases of disease or trauma and for the support and immobilization of ligamentous and muscular structures in instances of sprains and strains, it is necessary to encase the limb in a partially or completely surrounding rigid form or cast. The immobilized limb may be encased in such rigid structure for long periods of time, frequently as much as 6 weeks or more.

There are two major considerations for a cast. The first consideration concerns the formation of the cast. A satisfactory cast material should be easily handleable, should not have properties which deleteriously affect the limb, particularly the skin, should have a reasonable setting time or work life, so as to allow a reasonable period of time in which to mold the cast material about the limb, should be flexible during application to the limb so as to readily assume the shape of the limb, should be free of offensive or noxious solvents or other chemicals, and should set within a relatively short time under relatively mild conditions. In addition, it is desirable that a minimum of equipment should be involved in formation of the cast. Also it is desirable that during the forming of the cast the material does not generate an uncomfortable exothermic reaction, and that upon drying, curing or setting up it has a negligible shrinkage factor.

The second consideration concerns the properties of the cast after it is formed. Desirably, the cast should be of a light weight material so as to minimize the inconvenience to the wearer, porous so as to allow the underlying skin to breathe and not become macerated or otherwise irritated, should have sufficient structural strength so as to retain its structure under normal usage, should be sufficiently sturdy to maintain the joint or limb in the immobilized position and protect the joint or limb from jars, and should be easily removable. An optimum cast should also be water-proof, (i.e., the impregnated fabric material itself should not absorb and retain water), be as x-ray transparent as possible, be highly impact and abrassion resistant, and should exhibit a versatility to be reformed, and repaired after the initial cast is formed in place.

Because of the numerous and varied requirements for an orthopedic cast material, none of the presently known immediately available cast materials provide all or substantially all of the properties indicated above.

2. Description of the Prior Art

U.S. Pat. No. 3,692,023 describes the use of polycaprolactone as a cast material employing permeable or porous base webs impregnated with a polymer. See also U.S. Pat. Nos. 3,592,190, 2,301,426, 2,616,418, 3,420,231, 3,490,444, 3,592,190, 3,604,413.

SUMMARY OF THE INVENTION

A bandage or wrapping of an orthopedic cast comprising a large mesh flexible fabric carrier (e.g., large mesh cotton knit) impregnated with a polycaprolactone polymer (or other resin have substantially the same or equivalent property and behavorial characteristics as hereinafter more fully identified) to provide a relatively thick coating of the polymer while retaining substantially large openings in the mesh. The resulting coated fabric is semi-flexible, capable of being wound into a cylindrical package, and upon heating above the softening point of the polymer softens to a highly flexible or pliable and readily moldable wet. The web is readily formable by the hands and may be applied without protective covering and is not normally uncomfortable to the patient. The formed orthopedic cast rapidly cools to a hard durable porous cast, which is light and stable under normal usage conditions. The cast is easily removed by utilizing conventional cast cutting or sawing techniques and equipment.

BRIEF DESCRIPTION OF THE DRAWINGS

FIG. 1 is a fragmentary, full scale plan view of a cotton knit carrier before impregnation with the resin according to this invention;

FIG. 2 is the same as FIG. 1 after impregnation with the resin and showing how the mesh openings need not necessarily be maintained in perfectly square or rectangular shape to provide a satisfactory bandage for forming an orthopedic cast.

FIG. 3 is an enlarged view of the knit carrier shown in FIG. 1.

FIG. 4 is an enlarged view of the impregnated carrier shown in FIG. 2.

FIG. 5 is a diagrammatic view showing one method of fabricating a resin impregnated bandage embodying the invention.

DESCRIPTION OF SPECIFIC EMBODIMENTS

A novel highly advantageous material is provided for forming orthopedic casts. A fabric web is employed having relatively large openings and relatively heavy strands. Preferably, the strands are of a loose weave or knit, so as to be porous and subject to at least partial impregnation by the polymeric material. The web carrier serves as a structural element in the final product and is coated with at least an equal weight of the polymeric composition, and preferably a greater weight of the polymeric composition.

In describing the subject invention, the elements of the invention will be described as follows: (1) the carrier material; (2) the polymeric composition; (3) a method of preparing the orthopedic cast forming bandage; and (4) the orthopedic cast forming bandage.

Carrier Material

Referring particularly to FIGS. 1 and 3, the carrier material is a flexible large mesh fabric preferably knit defining a lattice of relatively large openings 3. The smallest dimension of the openings will generally be at least 0.015 sq. in. and preferably a minimum of 0.022 sq. in., about 0.034 sq. in. and generally not exceeding 0.25 sq. in., more usually not exceeding 0.050 sq. in. The openings may be of any configuration, such as square, polygonal, or the like. The opening shall be large enough so that in the finished product the polymer composition preferably does not form air impervious windows across the openings.

The strands 2 of the carrier which define the openings are preferably formed of relatively coarse, bulky, staple, porous, low density and thermal insulating material such as heavy yarn of 5 to 15 twist and having a raw diameter of at least 0.013 in., preferably about 0.015 in. and generally not exceeding 0.040 in., and when including the fluff or fuzz around the yarn strands at least 0.030 in., preferably a minimum of 0.050 in., about 0.075 in. and generally not exceeding 0.200 in. and more usually not exceeding 0.100 in.

Materials which may be used include cellulosic materials, such as cotton, synthetic materials, such as acrylates and nylon, or combinations thereof. For the most part, organic materials are employed, rather than more thermal conductive inorganic materials, such as glass fibers. Some significant factors concerning the material are that the material be a thermal insulator, that it provide structural stability to the final product, that it allow for molding to form the orthopedic structure, that it is wettable by the polymer composition, and that it is stable under normal usage. By way of more specific example, the low density strands of bulky Reschael type knits formed of staple fibers of cotton and defining naturally occurring multitudinous voids provides a desirable carrier material. A knit of the Reschael type inherently provides a highly flexible carrier material.

Preferably, the material should be substantially free of additives which may interfere with the bond between the polymer and the fiber. Cellulosic materials are preferably scoured to remove any binders or lubricants inhibiting the wetting properties of the polymer or other possibly deleterious additives.

Polymer Composition

While for the most part, poly-ε-caprolactone is commercially available and therefore the product of choice, other compositions resembling the properties of the polycaprolactone have been reported in the literature and to that extent could be employed to replace the polycaprolactone. See U.S. Pat. No. 3,692,023. However, for the purposes of describing a preferred embodiment of this invention, only the poly-ε-caprolactone will be referred to and is to be considered illustrative of this family of polymers. For purposes of convenience, the formula set forth in the aforestated patent is repeated with its definitions as inclusive of the tyes of polymers which may be employed.

These polymers are characterized by the recurring unit.

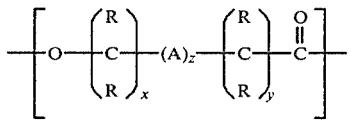

wherein each R, individually, is selected from the class consisting of hydrogen, alkyl, halo and alkoxy; A is the oxy group; x is an integer from 1 to 4; y is an integer from 1 to 4; z is an integer of zero or more; with the provisos that (a) the sum of $x+y+z$ is at least 4 and not greater than 7, and (b) that the total number of R variables which are substituents other than hydrogen does not exceed 3, preferably does not exceed 3 per unit. Illustrative R variables include methyl, ethyl, isopropyl, n-butyl, sec-butyl, t-butyl, hexyl, chloro, bromo, iodo, methoxy, ethoxy, n-butoxy, n-hexoxy, dodecoxy, and the like. It is preferred that each R, individually, be hydrogen, lower alkyl, e.g. methyl, ethyl, n-propyl, isobutyl, and/or lower alkoxy, e.g. methoxy, ethoxy, propoxy, n-butoxy, and the like. It is further preferred that the total number of carbon atoms in the R constituents does not exceed twenty.

The polymers which are employed with normally have a molecular weight of at least about 30,000 weight average molecular weight and preferably about 40,000 weight average molecular weight will have reduced viscosities as reported in the aforementioned patent of at least about 0.3 and generally not exceeding about 15, commonly above about 0.5 and up to about 10.

Small amounts, generally not exceeding 15 weight percent, more usually not exceeding 10 weight percent, and preferably from about 3 to 8 weight percent of inert insulative fillers may be included in the polymer composition. Such fillers include titanium dioxide, talc, magnesium or calcium carbonate, clay or other suitable inorganic or organic materials.

In the present invention the polymer should thermally soften at or above 125° F. and below about 180° F., and preferably between 145°–165° F.

Method of Making Orthopedic Cast Forming Bandage

Turning now to FIG. 5, a roll 10 of the appropriate knitted or loose carrier woven webbing 12 is provided. The webbing 12 is passed under first tank roller 14 and immersed in coating solution 16.

Various coating solutions may be employed having varying concentrations of polymer and fillers. A convenient volatile solvent for the polymer is used, for example, a halocarbon such as methylene chloride. A formulation which was found to be satisfactory is a mixture 95 weight percent PCL-700, a poly-ε-caprolactone having a weight average molecular weight of about 40,000 (available from Union Carbide) and 5 weight percent titanium dioxide. The composition is mixed with methylene dichloride to provide a mix having from about 5% to 50% solids and preferably 10% to 20% solids, the solids content generally being dictated by the workable viscosity required. It will be understood that coating techniques may be employed, such as hot melt coatings, where a 100% solids content is used.

The initially coated webbing is then passed between adjustable trunnion rolls 17 and past an air knife 18 and thence circuitously through oven 19 passing over rollers 20 adjacent the upper regions of the oven 19. The air knife 18 seves to blow out any polymer windows which may have formed in passing through the wet polymer solution 16, and the air knife also assists in the drying of the polymer applied to the wet carrier 12. The webbing is passed through the drying oven 20 is dried at an elevated temperature preferably around 180° F. Where one coat does not give a sufficiently thick and heavy coating of polymer, the knit fabric webbing 12, as shown in FIG. 5, is subjected to a repeat process of reimmersion in a polymer solution and subsequent drying. Corresponding parts of the equipment involved in the repeat process are numbered correspondingly to those parts already described but are suffixed by the letter "a" to distinguish them in the drawings.

A release film of polyethylene or similar material from an unwind roll 22 may be employed in forming the take-up roll 23 of the impregnated web 12 if the roller bandage layers adhere to each other during rolling or when the roll is heated to working temperature prior to its use in the making of an orthopedic cast as more specifically described hereinafter.

In the preferred embodiment the diameter of the impregnated strands 2a of the web 12 (and as shown in FIGS. 2 and 4) were measured in the range of between approximately 0.010 in. to 0.260 in. and generally between 0.075 in and 0.160 in.

The size of the openings 3a (as shown in FIGS. 2 and 4) of the impregnated web should generally be in somewhat lower range of area than given previously with respect to the dimension of the openings of the unimpregnated carrier material shown in FIGS. 1 and 3. The smallest dimension of the coated opening will generally be at least 0.010 sq. in., preferably a minimum of 0.020 sq. in., about 0.026 sq. in., generally not exceeding 0.250 sq. in. and usually not exceeding 0.050 sq. in. The shape of the openings shown in the impregnated web are disclosed as being in the form of a non-rectangular parallelogram as distinguished from the near square shaped openings of the unimpregnated knife carrier of FIGS. 1 and 3. Such variation in shape between the uncoated and coated carrier may result from the manner in which the carrier is handled during the coating process. In manufacturing the impregnated web according to the process described in reference to FIG. 5 and without utilizing rather special web tracking and handling equipment, it was found that the web could be better handled through the impregnation and oven drying process by running the fabric with the strands oriented parallel and perpendicular to the line of travel of the material through the equipment. Where the carrier material is originally oriented in a diagonal direction with respect to the strands, it may be desirable to cut the material on a bias and run it through the coating process so that the strands are substantially parallel and perpendicular instead of diagonal to the line of travel. Such an orientation will give a more rectangular finished product.

However, the disclosure of FIGS. 2 and 4 are made to indicate that the orientation during coating is not important and that in order to provide an entirely satisfactory bandaage it is not necessary that the openings be square or rectangular. It is important, however, that the openings after coating be of substantial area ranging for example between not less than 0.010 sq. in. to not more than 0.25 sq. in. and more preferably between 0.20 sq. in. and 0.050 sq. in. and around 0.026 sq. in.

As earlier noted it is important that the openings be large enough so that when a cast is formed by spirally wrapping and overlapping the material around the injured limb, that air passages through the thickness of the cast will be maintained to permit the underlying skin of the patient to breathe and to permit volatilization and dissipation of moisture from the interior of the cast.

When utilizing a Raschael type knit carrier formed of low density, staple fiber, bulky cotton strands as hereinabove desribed, and by utilizing the process of polycaprolactone polymer impregnation of said knit cotton carrier described in reference to FIG. 5, the following physical or mechanical characteristics of the impregnated web 12 (other than those characteristics already specified) have been observed:

1. Although both the polycaprolactone polymer and the cotton yarn have individual specific gravities in excess of the specific gravity of water which would lead to the apparently obvious conclusion that a mere combination of the two materials (i.e., impregnating the cotton yarn with the polymer) would result in a structure that would sink in water, the fact of the matter is that the final impregnated web 12 (as herein described) will float on water indicating that the specific gravity of the combined materials is less than the mere sum of the specific gravities of the two materials (polymer plus cotton yarn) divided by 2.

The apparent explanation for this observable fact is that upon magnified visual inspection of the impregnated strands 2a shows the existence of air voids still existing in the body of the cotton yarn where complete wetting and filling by the polymer has not occurred. It is theorized and believed, that this type of structure contributes materially to the utility and practical operability of the impregnated web as a suitable orthopedic cast bandage material. More specifically, it is known that air pockets fundamentally form relatively good heat insulating zones, and it is further known that the better the heat insulating qualities of a body the slower will be the rate of dissipation of stored heat therefrom. It is therefore reasoned that in respect of the intended and practical use of the present invention, the existence of air voids (heat insulating zones) in the web provides the unexpected advantages of providing a longer "working time" with the material and accounts for the fact that a rolled bandage of such material can be immediately removed from a hot water bath of over 165° F. and handled comfortably in the ungloved and bare hands of a physician user without his experiencing any discomfort as might be expected in handling such a relatively heated object. By "working time", and as will hereinafter be described, is the time that a physician has to remove a bandage roll from a hot water bath and unwind it will skill and care in a still softened and pliant condition around a patent's limb to form and mold an orthopedic cast.

Contributing also to the heat insulating properties of the impregnated web 12 (according to the present invention) is the use of an organic carrier material, such as cotton, which inherently is a relatively good heat insulator. In this connection, other resin impregnated orthopedic cast bandages on the market today utilize a glass fabric carrier which is not only less x-ray transparent, but is a relatively good heat conductor and would not provide the optimum advantages of heat insulating properties in the environment of the present invention as herein described.

2. The impregnated web 12 made according to the process, and using the polymer and fabric materials specifically described herein, has a measured or determinable ratio of approximately 4:1 polycaprolactone polymer weight to cotton yarn fabric weight, although this ratio may be varied substantially to produce reasonably satisfactory bandages within the range of 2 to 5:1 resin weight to fabric carrier weight.

Orthopedic Cast Forming Bandage and Use Thereof

A typical bandage formed from the impregnated and dried web 12 manufactured according to the process hereinabove described in reference to FIG. 5 of the drawings may be approximately 6 feet long and 3 inches wide in roll form with a parting film of sheet polyethylene separating adjacent layers of impregnating fabric in the roll.

In using the bandage to make an orthopedic cast it is convenient simply to immerse the rolled bandage in a vessel of hot water at a temperature above the thermal softening point of the polymer. In a bandage utilizing the preferred poly-ε-caprolactone polymer, the same has been found to soften readily when introduced into hot water at about 155°–165° F. Approximately two minutes in the hot water bath is sufficient to bring the web to a readily moldable state. While warm air or oven heat or the like can be used at the heat source to soften the polymer, the water bath is preferred because of its ability to rapidly and uniformly contact and heat all areas of the rolled bandage to uniform temperature. When removed from the water, the bandage can be readily wrapped about a limb without requiring any protective covering of the user's hands. When the usual normal underlying stockinette or padding is employed, there is no discomfort on the part of the patient. The heat softened and pliant bandage can be twisted, gathered, formed, re-formed, molded, rolled and unrolled as desired, there being ample time for the bonding between adjacent layers and the formation of the cast. Any release film may be peeled off and discarded as unwinding of the bandage proceeds. The cast may be allowed to cool and if desired, the rate of cooling can be enhanced by applying cold water compresses over the cast. Air cooling or other means is employed to increase the rate of hardening.

The resulting cast has a number of desirable feature. It is sufficiently transparent to x-rays, so that close to skin quality x-rays can be achieved. This means lower x-ray voltage may be employed as compared to other cast materials, such as plaster. The cast is light weight and a strong structure can be achieved with as little as 2 layers of the material. Channels are retained, so that the skin is able to breathe through the cast and marceration over the normal period of time for which the cast is worn is not observed. Strong bonding is obtained between the layers of the webbing, so that the cast does not come apart. In addition, the cast can be immersed in water and because of the porosity of the cast, the water will evaporate and the skin underneath the cast will retain its healthy condition.

By employing a heavy webbing with large openings and a relatively large proportion of polymeric composition, the polymeric composition remains moldable for a substantially long period of time. For example, a bandage roll of 6 feet in length upon heating in water of about 125°–165° will remain soft and bondable for a period of at least 30–45 seconds at room temperature. A cast made of a wound series of 3 rolls for example will remain hand pressure moldable or formable as a mass for approximately 3–4 minutes after application of the third roll. Thus, once the composition has reached its softening point, it is easily workable over a reasonable time which is required in forming the cast and insuring the proper positioning. The heavy strands of the web provide structure to the material and remain in place when positioned, so as to insure that on hardening the immobilized limb is held in the desired position.

During use, the cast has good wet strength and does not deteriorate upon repeated immersions in water, such as during swimming or taking showers or baths. In addition, the cast is highly abrasion resistant and capable of sustaining substantial impact. The cast provides protection for the injured limb and can be used in most situations normally encountered by the wearer.

Finally, the cast is readily removable as by cutting with a conventional vibrating sawtooth disc. A cast once formed in place over an injured limb can also be readily reformed, repaired, and in many instances re-used. For example, if a patient complains of a discomforting localized pressure point exerted by the cast, the cast can be reformed to ease the pressure merely by applying to it hot towels (or other type of heat) to cause the impregnated material to soften and be manually manipulated and molded to desired configuration.

In situations where it is necessary to cut out a plug to form a window in a cast for the physcan to observe or treat an underlying wound, the plug cut-out plug may be readily replaced simply by re-heating it and re-inserting it back in the window hole. If desired the plug can be more securely held in place by wrapping one or two layers of pre-softened new bandage material around the cast and overlying the re-inserted plug.

It is also possible in some instances to re-use either a single or double slit cast after its entire removal from a limb. This can be done merely by reheating in water or otherwise the removed cast parts and replacing and reforming them on the patient's limb, whereafter another layer or two of new bandage material can be wrapped around the original parts to hold them securely in place.

It will further be appreciated that the term orthopedic "casts" as used herein is also meant to include where applicable, the forming of splints and braces.

Further, although one manner of making and impregnating carrier 12 has been described in particular reference to FIG. 5 of the drawing, it is contemplated that the fabric carrier an be impregnated by other well known processes such as by hot-melting the powderous resin on the carrer, or by powder coating the carrier by passing the carrier one or more times through a fluidized bed of resin powder one or more times, and after each pass heating the material to cause the powder to fuse and bond itself to the carrier strands.

Although the foregoing invention has been described in some detail by way of illustration and example for purposes of clarity of understanding, it will be obvious that certain changes and modifications may be practiced within the scope of the appended claims.

We claim:

1. A bandage material for forming in place an orthopedic cast, comprising a pliant, large mesh fabric carrier formed from a knit having bulky strands of high structural stability and low density, each strand being formed from a plurality of fibers, said strands being porous and of relatively bulky and high heat insulating material, the fabric carrier having openings of relatively large transverse dimension, the strands having a raw diameter of between 0.013 and 0.040 inches, each strand being coated and only partially impregnated with a polymer composition having a heat softening point of not less than 125° F. and not greater than 165° F., said polymer coated strands defining openings having an area of not less than 0.020 square inches and not greater than about 0.25 square inches, whereby said openings are sufficiently large so that the polymer composition does not form air impervious blocks across the openings, said coated strands being sufficiently large so as to have a plurality of air voids providing increased insulating properties for said bandage material after the strands have been partially impregnated with said polymer composition.

2. A bandage material according to claim 1 wherein the openings are approximately 0.025 sq. in.

3. A bandage material according to claim 1 wherein the outside fluff diameter is between 0.030 in. and 0.20 in.

4. A bandage according to claim 3 wherein the carrier is a cotton knit formed of staple fiber.

5. A bandage according to claim 1 wherein said carrier comprises a Raschel type substantially cotton knit of staple fiber bulky strands.

6. A bandage according to claim 1 wherein the polymer coated strands have a diameter between 0.010 to 0.260 in.

7. A bandage according to claim 1 wherein the coated strands have a diameter between 0.075 in. and 0.160 in.

8. A bandage according to claim 1 where the polymer composition comprises a solid crystalline cyclic ester polymer having at least a major amount of recurring structural units of the formula:

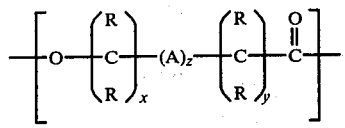

wherein each R, individually, is selected from the group consisting of halogen, alkyl, halo and alkoxy; A is the oxy group; X is an integer from 1 to 4; Y is an integer from 1 to 4; Z is an integer of 0 or 1; provided that (a) the sum of X plus Y plus Z is at least 4 and not greater than 7, and (b) that the total number of R variables which are substituents other than hydrogen does not exceed 3.

9. A bandage according to claim 8 and wherein said polymer composition comprises in major proportions a poly-S-caprolactone polymer.

10. A bandage according to claim 9 wherein the poly-ε-caprolactone polymer has a molecular weight average of at least 30,000.

11. A bandage according to claim 10 wherein the molecular weight of the poly-ε-caprolactone is about 40,000.

12. A bandage material for forming in place an orthopedic cast, comprising a pliant, large mesh fabric carrier having a high structural stability and Rascheal type substantially cotton knit of staple bulky strands, each strand being formed from a plurality of fibers and being coated and only partially impregnated with a polymer composition having a heat softening point of not less than 125° F. and not greater than 165° F., each coated strand having a diameter between about 0.010 to about 0.260 inches, said polymer coated strands defining openings having an area of not less than about 0.020 square inches and not greater than about 0.25 square inches, whereby said openings are sufficiently large so that the polymer composition does not form impervious blocks across the openings, said strands having a raw diameter of between 0.013 inches and 0.040 inches to cause the coated strands to be sufficiently large so as to have a plurality of air voids providing increased insulating properties to said bandage material.

13. A bandage according to claim 12 wherein the polymer composition comprises in major proportions a poly-ε-caprolactone polymer having a molecular weight average of at least 30,000.

* * * * *